United States Patent [19]

Jones

[11] Patent Number: 4,689,309

[45] Date of Patent: Aug. 25, 1987

[54] TEST DEVICE, METHOD OF MANUFACTURING SAME AND METHOD OF DETERMINING A COMPONENT IN A SAMPLE

[75] Inventor: James E. Jones, Elkhart, Ind.

[73] Assignee: Miles Laboratories, Inc., Elkhart, Ind.

[21] Appl. No.: 781,905

[22] Filed: Sep. 30, 1985

[51] Int. Cl.$^4$ ................. G01N 33/52; G01N 33/66
[52] U.S. Cl. ..................... 436/95; 422/56; 427/397.7; 435/805; 436/169
[58] Field of Search ............ 436/95, 169; 422/56, 422/57; 435/805, 14; 427/397.7

[56] References Cited

U.S. PATENT DOCUMENTS

| | | | |
|---|---|---|---|
| 3,418,083 | 12/1968 | Rey et al. | 436/95 X |
| 3,635,679 | 1/1972 | Bloch et al. | 436/169 X |
| 4,003,707 | 1/1977 | Lubbers et al. | 436/163 X |
| 4,327,203 | 4/1982 | Deichert et al. | 526/279 |
| 4,495,361 | 1/1985 | Friends et al. | 556/419 |
| 4,587,101 | 5/1986 | Marsoner et al. | 422/56 |

FOREIGN PATENT DOCUMENTS 1161346  1/1984  Canada ................................ 436/79

*Primary Examiner*—Barry S. Richman
*Assistant Examiner*—Michael S. Gzybowski
*Attorney, Agent, or Firm*—Roger N. Coe

[57] ABSTRACT

A method of manufacturing the test device and method of determining the presence and relative concentration of a component in a test sample. The device includes a carrier matrix incorporated with a reactant system capable of interacting with a sample component to produce a detectable response. For home use, the reactant system produces a visibly detectable response. The carrier matrix of the device comprises a new and improved whole blood compatible, glucose-permeable strip or layer of a polymerizable silicone material. A reactant system is homogeneously mixed into the polymerizable carrier matrix prior to complete curing of the matrix, and the matrix then is cured to hold the reactant system homogeneously throughout the carrier matrix in a known concentration while maintaining matrix penetrability of the predetermined component after complete curing of the carrier matrix. The carrier matrix is formed from a dispersion of a polymerizable silicon-containing compound applied in an incompletely cured from in a liquid carrier containing a homogeneously mixed reactant system.

38 Claims, 4 Drawing Figures

TEST DEVICE, METHOD OF MANUFACTURING SAME AND METHOD OF DETERMINING A COMPONENT IN A SAMPLE

BACKGROUND OF THE INVENTION

A. Field of the Invention

The present invention relates to a new and improved test device for the assay of fluids to determine the presence of a chemical compound, such as glucose; lower alcohols, such as ethanol; cholesterol; and uric acid and, particularly to a new and improved method and device for measuring glucose. More particularly, the present invention relates to a new and improved whole blood compatible, glucose test strip including a reactant system incorporated into a carrier matrix made from a silicon-containing polymerizable material permeable to glucose and to a new and improved method of quantitatively measuring glucose in whole blood.

B. Description of the Prior Art

Devices that measure fluctuations in a person's blood sugar, or glucose levels have become everyday necessities for many of the nation's seven million diabetics. Because this disorder can cause dangerous anomalies in blood chemistry and is believed to be a contributor to vision loss and kidney failure, most diabetics need to test themselves periodically and adjust their glucose count accordingly, usually with insulin injections. Patients who are insulin dependent—about 10% to 15% of diabetics—are instructed by doctors to check their blood-sugar levels as often as four times daily.

For years the solution for diabetics was one of several urinanalysis kits that, despite repeated improvements, provide imprecise measurements of glucose in the blood. Examples of early urine testing for glucose are described in U.S. Pat. Nos. 2,387,244 and 3,164,534. Later, reagent strips for urine testing were developed. Testing of urine for glucose, however, is limited in accuracy particularly since the renal threshhold for glucose spillage into the urine is different for each individual. Moreover, sugar (glucose) in urine is a sign that the glucose was too high several hours prior to the test because of the time delay in glucose reaching the urine. Readings taken from the urine, therefore, are indicative of the glucose level in the blood several hours before the urine is tested.

More accurate readings are possible by taking readings directly from blood to determine current glucose levels. The advent of home blood tests is considered by some to be the most significant advance in the care of diabetics since the discovery of insulin in 1921. Home blood glucose testing was made available with the development of reagent strips for whole blood testing. The reagent strip includes a reactant system comprising an enzyme, such as glucose oxidase, capable of catalyzing the oxidation reaction of glucose to gluconic acid and hydrogen peroxide; an indicator or oxidizable dye, such as o-tolidine; and a substance having peroxidative activity capable of catalyzing the oxidation of the indicator. The dye or indicator turns a visually different shade of color depending upon the extent of oxidation - dependent upon the concentration of glucose in the blood sample.

The reactions occurring in the reaction system are represented as follows:

Glucose oxidase

Substance having peroxidative activity $$H_2O_2 + \text{oxidizable dye} \longrightarrow \text{Oxidized dye} + H_2O$$
(color change)

Extant reagent strips generally include a matrix material such as a bibulous, e.g., cellulosic, material impregnated with the reactant system capable of reacting with glucose as described above, and a matrix overcoating material capable of filtering out blood cells to prevent the blood cells from staining the matrix material. The overcoating material is necessary so that the colored blood cells do not interfere with proper determination of the dye color produced by dye oxidation. The colored blood cells can be wiped or washed off of the overcoating material before color analysis. The overcoating blood cell filter material was difficult to apply and it was difficult in manufacturing to provide a closely bonded, uniform coating. Examples of reagent strips of this type are described in U.S. Pat. Nos. 3,164,534 and 3,092,465. A breakthrough in self-care came in 1979, when the Ames Division of Miles Laboratories brought out its VISIDEX home blood testing kit. The VISIDEX home blood testing kit consists of disposable chemically coated plastic strips. When blood drawn by pricking a finger is placed on one of these strips, the resulting color change indicates the glucose content in the blood based on light reflection from the blood-contacted reagent strip.

The most significant advantages of the current technology available for home use reagent strips are low cost (roughly fifty cents per use) and a short, e.g. one minute, response time. There are significant problems with reagent strips, however. One of the most significant problems with extant reagent strips for whole blood glucose testing is that the strips are impregnated with an indeterminable amount and concentration of the reactant system. Further, the reactant system impregnated reagent strips cannot be manufactured having a completely homogeneous concentration of reactants, because of the incompletely homogeneous chemical uptake of the matrix, e.g., bibulous materials. Further, because of the imprecise nature of impregnation and differences in chemical uptake through the bibulous material volume, the concentration of reactants is imprecise, and varies throughout the strip volume. Further, blood wiped or washed from the surface of bibulous materials to obtain a more accurate visual indication of change resulting from glucose reaction, easily can change the surface of the bibulous material unless coated with a protective coating of material capable of filtering out hemoglobin or other coloring bodies found in whole blood making it much more difficult to make a color chart comparison and an accurate glucose concentration determination.

Silicone polymerized materials have not been used in the prior art as glucose-permeable matrix materials. Although prior art silicone rubbers are whole blood compatible and oxygen permeable, they are not glucose permeable -an essential function of a glucose reactant matrix material. An example of an electrode membrane assembly with a silicone rubber secondary membrane is disclosed in U.S. Pat. No. 3,979,274, but such material is not glucosepermeable.

In addition to whole blood, there are other body fluids from which glucose can be measured. Published data indicate that sweat is an ultrafiltrate of blood with a low, variable glucose concentration. The literature indicates that glucose concentration in the interstitial extracellular space and intramuscular or subcutaneous locations is lower than blood glucose but this is believed to be a good measure of the blood glucose. Thus, glucose reaches the underside of the skin in potentially useful amounts.

Conventional sensors for measuring glucose in sweat require withdrawing a sample or employing elaborate procedures or testing equipment. Examples of conventional sensors are disclosed in U.S. Pat. Nos. 4,044,772; 4,195,641; and 4,329,999. There is a need for a noninvasive sensor for measuring glucose in a body fluid such as sweat. The preferred sensor would not include elaborate equipment or require elaborate procedures. In accordance with the present invention, the reagent strips disclosed herein are sufficiently glucose permeable and produce a detectable color change upon contact with body sweat.

SUMMARY OF THE INVENTION

An object of the present invention is to provide a new and improved method and test device for determining the relative concentration of a chemical compound in a liquid.

Another object of the present invention is to provide a new and improved glucose-reactive test device for reaction with glucose in a test fluid to produce a visible change, such as a change in color, of the test device, indicative of the glucose concentration in the test fluid.

Still another object of the present invention is to provide a new and improved test device and method of manufacturing the test device including a carrier matrix having incorporated therein during manufacture thereof, a reactant system capable of interacting with a chemical compound in a test sample, wherein the carrier matrix comprises a polymerizable silicon-containing compound dispersed in a liquid carrier removable in an amount of at least 5% by weight during polymerization in layer form.

A further object of the present invention is to provide a new and improved test device and method of manufacturing the test device having a reactant system incorporated into a carrier matrix permeable to glucose, oxygen, cholesterol, lower alcohols, such as ethanol, and uric acid, for determining the relative concentration or presence of any of these compounds present in an assay liquid.

Another object of the present invention is to provide a whole blood compatible reagent strip comprising a carrier matrix comprising a polymerizable silicon-containing compound capable of relatively homogeneous mixture with a reactant system prior to curing and permeable to glucose and oxygen after curing.

Another object of the present invention is to provide a new and improved test device and method of manufacturing the test device for sensing the presence of a chemical compound in a liquid, where the chemical compound is capable of permeating a polymeric carrier matrix and capable of reacting with a reactant system incorporated in the carrier matrix during manufacture prior to complete curing of the carrier matrix.

A still further object of the present invention is to provide a new and improved whole blood glucose reagent strip capable of incorporation of a reactant system into the carrier matrix during manufacture to achieve a reagent strip of new and unexpected precision in glucose response.

Another object of the present invention is to provide a new and improved test device, and method of manufacturing the test device, formed from a polymerizable silicon-containing compound dispersed in a liquid carrier removable from the test device in an amount of at least 5% by weight during polymerization of the carrier matrix in layer form.

Another object of the present invention is to provide a new and improved reagent strip, capable of interacting with a predetermined liquid chemical component in an assay medium, having a reactant system carrier matrix comprising a cured polymer layer permeable to the predetermined liquid chemical component of the assay medium.

Another object of the present invention is to provide a new and improved test device for quantitative analysis of glucose.

Briefly, the present invention is directed to a new and improved test device, method of manufacturing the test device, and method of determining the presence and relative concentration of a component in a test sample. The device includes a carrier matrix incorporated with a reactant system capable of interacting with a sample component to produce a detectable response. For home use, the reactant system produces a visibly detectable response. The carrier matrix of the device of the present invention comprise a new and improved whole blood compatible, glucose-permeable strip or layer of a polymerizable silicone material. A reactant system is homogeneously mixed into the polymerizable carrier matrix prior to complete curing of the matrix, and the matrix then is cured to hold the reactant system homogeneously throughout the carrier matrix in a known concentration while maintaining matrix penetrability of the predetermined component after complete curing of the carrier matrix.

A new and improved carrier matrix formed from a dispersion of a polymerizable siliconcontaining compound applied in an incompletely cured from in a liquid carrier containing a homogeneously mixed reactant system is applied by painting or any other means over a suitable substrate to form the test device into layer form. After formation into layer form, the polymerizable compound is cured to immobilize the reactant system while maintaining component permeability of the carrier matrix. The unique carrier matrix is whole blood compatible allowing the test strips to be home useable without the need for whole blood dilution. Since the test strips of the present invention are whole blood compatible, oxygen and glucose-permeable and screen out most interferants, the test strips yield more accurate and repeatable glucose responses enabling a more accurate visual determination of glucose concentration from a drop of whole blood. Another advantage of the test strips of the present invention is relatively high oxygen-permeability. High oxygen-permeability of the membrane provides a linear response in the relationship of glucose concentration and visible glucose interaction response when the glucose interaction is one wherein oxygen participates in the reactant system interaction, over the full useful range of glucose concentration. The linear response provides increased response, accuracy and reliability. The linear response also allows higher and lower dynamic readings than available in the prior art. Readings at these extreme levels are the most critical for diabetics.

BRIEF DESCRIPTION OF THE DRAWINGS

The above and other objects and advantages and novel features of the present invention will become apparent from the following detailed description of the preferred embodiments of the invention illustrated in the accompanying drawings illustrating the color change in the reagent strips of the example with time and glucose concentration. In all four figures, the reflectance measurements have been converted to K/S, as well known and disclosed in Kubelka, P. et al., Z. Tech. Phy. 12,593 (1931) and Kortam, G., "Reflectance Spectroscopy; Principles, Methods, Application", Springer-Uerlay; New York, 1969.

DETAILED DESCRIPTION OF THE PREFERRED EMBODIMENTS

In accordance with an important feature of the present invention it has been found that a dispersion of a polymerizable silicon-containing compound applied in an incompletely cured form as a silicon compound dispersed phase in a liquid carrier, the carrier being essentially insoluble in the dispersed phase and removable from the dispersion during curing, will dry and cure as a continuous layer, film or membrane having unexpectedly high glucose-permeability to function as a carrier matrix in a reagent test strip. The silicon-containing compound can be dispersed in the continuous phase as a monomer, oligomer, prepolymer, or incompletely cured polymer. The silicon compound, forming the carrier matrix, is mixed with a reactant system capable of interacting with a predetermined chemical compound of the test sample to produce a detectable response, and the matrix is cured in layer form and then cut into strips. The liquid carrier, removed during curing, such as by volatilization, should be included in an amount of at least 5% by weight of the dispersion, and preferably 10–90% by weight.

It has been found that the polymerizable silicon-containing compounds including monomers, oligomers, prepolymers, and incompletely cured polymers or mixtures thereof capable of polymerization or further polymerization in dispersed form will form cured layers when cured or polymerized in a dispersed layer upon removal of the continuous phase during curing to provide a layer or membrane having unexpectedly good oxygen and glucose-permeability. The polymerizable silicon-containing compounds, after dispersion in a continuous phase, such as by including an emulsifier, can be cured in any known manner during removal of the continuous phase, such as by evaporation of water from a water-continuous phase silicon emulsion or dispersion, as disclosed in the Johnson et al U.S. Pat. No. 4,221,688, incorporated herein by reference, or as disclosed in Elias U.S. Pat. No. 4,427,811, also incorporated herein by reference. Further, the dispersion of the silicon-containing compound can include a suitable curing catalyst or can be heat cured so long as the dispersion of the polymerizable silicon-containing compound is applied as a layer in the form of an incompletely cured dispersion and at least a portion of the carrier or continuous phase is removed from the dispersion during final curing. Without being limited to any particular mechanism, it is theorized that some alignment of the aggregating or polymerizing silicon-containing polymer molecules, during polymerization, occurs during final removal of the carrier to form micelles such that the aggregating silicon-containing polymer molecules are bound upon curing in a manner capable of permitting the permeation of glucose and oxygen between molecules while excluding glucose reaction interferants.

The silicon-containing compounds, useful in accordance with the invention are those which can be dispersed in an essentially insoluble liquid carrier, such as water, are polymerizable in the dispersed form, and result in a continuous film or layer upon curing.

In accordance with one embodiment of the present invention, the polymerizable silicon-containing compound is an organosiloxane, and particularly a diorganosiloxane comprising essentially a linear species of repeating diorganosiloxane units which can include small numbers of monoorganosiloxane units up to a maximum of about one monoorganosiloxane unit for each 100 diorganosiloxane units wherein the polymer chain is terminated at each end with silicone-bonded hydroxyls, as disclosed in Johnson et al. U.S. Pat. No. 4,221,688, hereby incorporated by reference.

In accordance with another important embodiment of the present invention, the polymerizable silicon-containing compound forming the carrier matrix comprises a continuous water phase and an anionically stabilized dispersed silicone phase wherein the silicone phase is a graft copolymer of a water soluble silicate and a hydroxyl endblocked polydiorganosiloxane. As disclosed in the Saam U.S. Pat. No. 4,244,849, such silicone emulsions having a pH within the range of from 8.5 to 12, are stable upon extended storage and result in a cured elastomeric continuous layer upon removal of water under ambient condition These silicone compounds are obtained from the interaction of hydroxyl end-blocked polydiorganosiloxanes and alkali metal silicates to form graft copolymers anionically stablized in aqueous emulsions at a pH of, for example, 8.5 to 12. If stability is not important, however, the pH is not critical. For example, the emulsion can be applied in layer form to manufacture the reagent strips as soon as the matrix components and reactant system are homogeneously dispersed.

The expression "hydroxyl endblocked polydiorganosiloxane" is understood to describe an essentially linear polymer of repeating diorganosiloxane units containing no more than small impurities of monoorganosiloxane units. The hydroxyl endblocked diorganosiloxane will therefore have essentially two silicon-bonded hydroxyl radicals per molecule. To impart elastomeric properties to the product obtained after removal of the water from the emulsion, the polysiloxane should have a weight average molecular weight ($M_w$) of at least 5,000. Polysiloxanes with weight average molecular weights below 5000, for example down to about 90, also are useful so long as the polymers form a continuous film or layer upon curing. Tensile strengths and elongations at break improve with increasing molecular weight with relatively high tensile strengths and elongations obtained above 50,000 Mw. However, high strength is not necessary for the polymer of the carrier matrix to be useful in the invention described herein. The maximum $M_w$ is one which can be emulsified or otherwise dispersed in a liquid carrier or continuous phase, such as water. Weight average molecular weights up to about 1,000,000 for the incompletely cured dispersed polysiloxane are expected to be practical for this invention. Upon curing, there is no upper limit to the molecular weight of the membrane. The preferred $M_w$ for the polymerizable dispersed siloxane is in the range of 1,000 to 700,000.

Organic radicals on useful hydroxyl endblocked polydiorganosiloxanes can be, for example, monovalent hydrocarbon radicals containing less than seven carbon atoms per radical and 2-(perfluoroalkyl)ethyl radicals containing less than seven carbon atoms per radical. Examples of monovalent hydrocarbon radicals include methyl, ethyl, propyl, butyl, isopropyl, pentyl, hexyl, vinyl, cyclohexyl and phenyl and examples of 2-(perfluoroalkyl)ethyl radicals include 3,3,3-trifluoropropyl and 2-(perfluorobutylmethyl). The hydroxyl endblocked polydiorganosiloxanes preferably contain organic radicals in which at least 50 percent are methyl. The preferred polydiorganosiloxanes are the hydroxyl endblocked polydimethylsiloxanes.

In accordance with one important embodiment of the present invention, the hydroxyl endblocked polydiorganosiloxane is employed as an anionically stabilized aqueous emulsion. For the purposes of this embodiment "anionically stabilized" means the polydrorganosiloxane is stabilized in emulsion with an anionic surfactant. The most preferred anionically stabilized aqueous emulsion of hydroxyl endblocked polydiorganosiloxane are those prepared by the method of anionic emulsion polymerization described by Findlay et al. in U.S. Pat. No. 3,294,725, hereby incorporated by reference to show the methods of polymerization and to show anionically stabilized emulsions of hydroxyl endblocked polydiorganosiloxanes. Another method of preparing hydroxyl endblocked polydiorganosiloxanes is described by Hyde et al in U.S. Pat. No. 2,891,920, hereby incorporated by reference to show the hydroxyl endblocked polydiorganosiloxanes and their method of preparation. These methods and others are known in the art.

An alkali metal silicate or colloidal silica can be included in the emulsified silicone composition for the preparation of extended storage stable matrix emulsions used in the invention. The alkali metal silicates preferred for use in the emulsions forming the glucose-permeable test strips of the present invention are water soluble silicates. The alkali metal silicate is preferably employed as an aqueous solution. Aqueous silicate solutions of any of the alkali metals can be employed such as lithium silicate, sodium silicate, potassium silicate, rubidium silicate and cesium silicate.

The colloidal silicas are well known in the art and many are commercially available and can be included in the dispersion for increased strength and storage stability. Although any of the colloidal silicas can be used including fumed colloidal silicas and precipitated colloidal silicas, the preferred colloidal silicas are those which are available in an aqueous medium. Colloidal silicas in an aqueous medium are usually available in a stabilized form, such as those stabilized with sodium ion, ammonia or an aluminum ion. Aqueous colloidal silicas which have been stabilized with sodium ion are particularly useful for forming an emulsion because the pH requirement can be met by using such a sodium ion stabilized colloidal silica without having to add additional ingredients to bring the pH within the range of, for example, 8.5 to 12. The expression "colloidal silica" as used herein are those silicas which have particle diameters of from 0.0001 to 0.1 micrometer. Preferably, the particle diameters of the colloidal silicas are from 0.001 to 0.05 micrometer.

The colloidal silica can be added to the anionically stabilized hydroxylated polydiorganosiloxane in the form of a dry powder or as an aqueous dispersion. The best method is to add the colloidal silica in the form of a sodium ion stabilized aqueous dispersion of colloidal silica. There are many such sodium ion stabilized aqueous dispersions of colloidal silica which are commercially available. These commercial colloidal silicas are usually available in aqueous dispersions having from 15 to 30 weight percent colloidal silica and having a pH in the range of 8.5 to 10.5.

Aqueous solutions of sodium or potassium silicate are well known and are commercially available. The solutions generally do not contain any significant amount of discrete particles of amorphous silica and are commonly referred to as water glass. The ratio by weight of $SiO_2$ to alkali metal oxide in the aqueous solutions of alkali metal silicates is not critical and can be varied within the usual range of about 1.5 to 3.5 for the sodium silicates and 2.1 to 2.5 for the potassium silicates. The aqueous alkali metal silicate solutions are particularly useful in preparing the emulsions of the present invention because the addition of the silicate solution often brings the pH of the emulsion within the range of about 8.5 to about 12, prior to addition of the reactant, color changing composition, so that additional ingredients are not necessary to adjust the pH of the emulsion. Of course, other aqueous alkali metal silicate solutions such as those prepared by hydrolyzing silicon esters in aqueous alkali metal hydroxide solutions can also be employed in the present invention.

In accordance with one embodiment of the present invention, the polymerizable siliconcontaining compound is dispersed by combining an aqueous solution of an alkali metal silicate and the polymerizable siliconcontaining compound in an emulsion so that a graft copolymer is formed as dispersed particles. The preferred procedure for preparing silicone emulsions is to add the alkali metal silicate to an anionically stabilized aqueous emulsion of one or more hydroxyl endblocked polydiorganosiloxanes, adjust the pH of the emulsion within the range of about 8.5 to 12, prior to addition of the reactant system, and then age the emulsion for a time period such that an elastomeric product is formed upon removal of the water under ambient conditions. In this embodiment, the pH of the emulsion containing dissolved silicate and dispersed hydroxyl endblocked polydiorganosiloxane is important to the formation of the emulsion. A pH of 8.5 to 12 maintains the alkali metal silicate dissolved so that sufficient graft copolymerization between the dissolved silicate and dispersed siloxane occurs during removal of the carrier (e.g., water) to produce an emulsion capable of providing polymerization or further polymerization of the siliconcontaining compound when deposited as a layer to form the test strips of the present invention. If the pH is lower than the stated range, silicic acid is formed from the alkali metal silicate. Silicic acid is unstable and rapidly polymerizes by condensation which can gel the emulsion. Since silicic acid formation is almost completely suppressed at a pH of 10 to 12 and the reaction between dissolved alkali metal silicate and dispersed siloxanes occurs more rapidly within the pH range of 10–12, this pH range is preferred for emulsions containing an alkali metal silicate. Otherwise, the pH of the silicon compound-containing emulsion with the reactant system incorporated therein, is maintained at a pH of about 7.5 to 11 or 11.5.

Silicone emulsions prepared by this silicate copolymerization embodiment are aged at a pH range of 8.5 to 12, with or without the reactant system incorporated therein, for a time period sufficient to allow interaction between the dissolved silicate and the dispersed siloxane so that an elastomeric product is formed upon removal of the water under ambient conditions, as disclosed in Saam U.S. Pat. No. 4,244,849 hereby incorporated by reference. The aging period is effectively reduced when an organic tin salt is employed in an amount of about 0.1 to 2 parts by weight for each 100 parts by weight of polydiorganosiloxane. The organic tin salts expected to be useful in the emulsions include mono-, di-and triorganotin salts. The anion of the tin salt employed is not critical and can be either organic or inorganic although organic anions such as carboxylates are generally preferred. Organic tin salts that can be employed include octyltin triacetate, dioctyltin dioctoate, didecyltin diacetate, dibutyltin diacetate, dibutyltin dibromide, dioctyltin dilaurate and trioctyltin acetate. The preferred diorganotin dicarboxylate is dioctyltin dilaurate.

The concentration of the polymerizable silicon-containing compound, e.g. the hydroxyl endblocked polydiorganosiloxane in the stabilized emulsion is not critical particularly since the water or other continuous phase carrier is removed during curing of the Si phase during film or layer formation of the reagent strips of the present invention.

The relative amounts of alkali metal silicates and hydroxyl endblocked polydiorgano-siloxane employed can vary over a considerable range. Preferred elastomer properties are obtained when 0.3 to 30 parts by weight silicate is employed for each 100 parts by weight siloxane.

Other useful polymerizable silicon-containing compounds for forming the dispersions useful in forming a continuous silicon-containing polymer carrier matrix having glucose-permeability in accordance with the present invention include the vinyl endblocked polydiorganosiloxanes dispersed together with an organosilicone compound having silicone-bonded hydrogen atoms, as disclosed in the Willing U.S. Pat, No. 4,248,751, hereby incorporated by reference. As disclosed in the Willing patent, these silicone compounds are generally dispersed by emulsifying the vinyl endblocked polydiorganosiloxane together with an organosilicone compound having silicone-bonded hydrogen atoms using water and a surfactant to form an emulsion and thereafter adding a platinum catalyst and heating the emulsion to form a crosslinked silicone.

The vinyl endblocked polydiorganosiloxane can be any of the polydiorganosiloxanes endblocked with diorganovinylsiloxy units and can be represented by the formula (CH$_2$=CH)R$_2$SiO(R$_2$SiO)$_x$SiR$_2$(CH=CH$_2$)

where each R is a monovalent hydrocarbon radical or a monovalent halogenated hydrocarbon radical and x is a representation of the number of repeating diorganosiloxane units in the polymer. The monovalent radicals can be any of those known in the art, but are preferably those with six carbon atoms or less. The preferred polydiorganosiloxanes are those wherein the monovalent organic radicals are methyl, ethyl, phenyl, 3,3,3-trifluoropropyl and mixtures thereof wherein at least 50 percent of the radicals are methyl radicals. The polydiorganosiloxane can be a single type polymer with the same kind of repeating diorganosiloxane units or with a combination of two or more kinds of repeating diorganosiloxane units, such as a combination of dimethylsiloxane units and methylphenylsiloxane units. A mixture of two or more polydiorganosiloxanes also is useful. The value of x is not critical since upon final curing in the dispersed layer, the value of x increases rapidly. The upper limit of polydiorganosiloxane which is suitable for this invention is limited only to the extent that it cannot be dispersed to form a homogenous dispersion to achieve a homogenous layer capable of forming a continuous layer upon complete curing.

In accordance with this vinyl-endblocked embodiment, the organosilicone compound or mixture of compounds dispersed with the polydiorganosiloxane is one which contains silicon-bonded hydrogen atoms. The organosilicon compound can be any compound or combination of compounds containing silicon-bonded hydrogen atoms useful as crosslinkers and providing an average of siliconbonded hydrogen atoms per molecule of organosiloxane compound of at least 2.1. Such organosilicon compounds are known in the art as illustrated in U.S. Pat. No. 3,697,473, which is hereby incorporated by reference. The preferred organosilicon compounds are those which are siloxanes made up of units selected from HSiO$_{1.5}$, R'HSiO, R'$_2$HSiO$_{0.5}$, R'SiO$_{1.5}$, R'$_2$SiO, R'$_3$SiO$_{0.5}$ and SiO$_2$ such that there is at least 2.1 siliconbonded hydrogen atoms per molecule. Each R' is preferably selected from an alkyl radical of 1 to 12 carbon atoms inclusive, phenyl and 3,3,3-trifluoropropyl.

The amount of vinyl endblocked diorganosiloxane and organosilicon compound can vary broadly in weight amounts because the unit of weight for each vinyl radical or silicon-bonded hydrogen atom will vary considerably. Such "units of weight" are determined by dividing the molecular weight by the number of vinyl radicals per molecule or number of SiH per molecule. Because the cross-linked molecules in the membrane are formed by the reaction between the vinyl radical of the polydiorganosiloxane and the silicon-bonded hydrogen atom (SiH) of the organosilicon compound, the amounts of each will depend upon the ratio of SiH to vinyl. The stoichiometry would suggest that about one SiH per vinyl is all that is needed, however, the reactivity of the SiH can vary significantly, as well as its availability for reaction. For this reason, the ratio of SiH to vinyl can vary beyond the stoichiometric amounts and still provide products capable of polymerizing in layer form to provide continuous glucose-permeable carrier matrix strips. The vinyl endblocked polydiorganosiloxane and organosilicon compound preferably are combined such that the ratio of SiH to vinyl can vary from 0.75/1 to 4/1, with the most perferred range of 0.75/1 to 1.5/1.

The platinum catalyst can be any of the platinum catalysts known to catalyze the addition of silicon-bonded hydrogen atoms to silicon-bonded vinyl radicals. Platinum catalysts can be any of the known forms, ranging from platinum as such or as deposited on carriers such as silica gel or powdered charcoal, to platinic chlorides, salts of platinum and chloroplatinic acid. The dispersibilty of the platinum catalysts in the siloxane can be increased by complexing it with vinyl-containing siloxanes such as described in U.S. Pat. No. 3,419,593.

The amount of platinum catalyst used should be such that there is at least 0.1 part by weight platinum per one million parts by weight of the combined weight of polydiorganosiloxane and organosilicon compound. Preferably, the amount of catalyst used is from 1 to 20 parts by weight platinum per million parts by weight of polydiorganosiloxane and organosilicon compound. Larger amounts of platinum can be used if economic considerations are not important.

For those cases where a platinum catalyst is included in the dispersion and a platinum catalyst inhibitor is desired to prevent complete curing prior to layering the dispersion for formation of the test device or reagent strip, there are many types of known inhibitors. These inhibitors retard or inhibit the activity of the platinum catalyst, but allow the platinum catalyst to become active at elevated temperatures, such as above 70° C. If the carrier in the dispersion is water, the selection of an inhibitor should be one which does not have its effectiveness destroyed by water or surfactants or it does not destroy the emulsion. Effective inhibitors include the acetylenic alcohols and other acetylenic compounds described in U.S. Pat. No. 3,445,420. Other platinum catalyst inhibitors are known as defined in U.S. Pat. Nos. 3,188,299, 3,188,300, 3,192,181, 3,344,111, 3,383,356, 3,453,233, 3,453,234 and 3,532,649. The dispersed composition can be heated for a period of time to partially cross-link the Si-containing compounds to form a stable emulsion of cross-linked particles dispersed in a carrier. After homogeneous mixing of the reactant system into the dispersion of carrier matrix, the dispersed mixture is applied onto a permanent (e.g., polystyrene, paper, glass, polyethylene, metal foil, polyethylene terephthalate) or removable support into layer form and the layer further cured to form a continuous, glucose-permeable sheet thereafter divided into thin strips.

Evaporation of the carrier from the carrier matrix can be assisted by a flow of dry air or other gas, either at ambient temperature or at an elevated temperature, by infrared heating or a combination of the various means. Care should be taken when accelerated means are used to evaporate the carrier, e.g. water, that the rapidly leaving water vapor does not produce undesirable discontinuities in the carrier matrix layer.

Other reinforcing materials useful for increasing the structural integrity of the cured carrier matrixes of the present invention include the copolymers disclosed in the Huebner et al U.S. Pat. No. 4,288,356, hereby incorporated by reference. The copolymers are emulsion polymerized and comprise free radical polymerized monomers selected from at least one unsaturated organic monomer and at least one unsaturated organosilicone monomer. The copolymers are made from 1 to 7 weight percent unsaturated organosilicon monomer and from 93 to 99 weight percent organic monomer. It is believed that any of the unsaturated organic monomers commonly used to form polymers through free radical polymerization can be used either by themselves or in combination; for example, styrene, methylmethacrylate, and vinyl chloride. The unsaturated organosilicon monomer can be an unsaturated silane, siloxane, or silazane that will copolymerize with the unsaturated organic monomer or mixture of unsaturated organic monomers used and will form SiOH under the conditions of an emulsion polymerization method used to produce the copolymer.

The unsaturated organosilicon monomer can be a silane of the formula $R'R''xSi(R''')_{3-x}$ where $R'$ is an olefinic unsaturated radical such as vinyl, allyl, acryloxypropyl, or methacryloxypropyl, $R''$ is an alkyl radical containing 1 to 4 inclusive carbon atoms or a phenyl radical, and $R'''$ is a hydrolyzable group such as -OR'',--OCOR'', or halogen, and x is 0, 1 or 2. The unsaturated organosilicon monomer can be a cyclic siloxane of the formula $(R'R''SiO)_a$ where $R'$ and $R''$ are as defined and a is from 3 to 6 inclusive. The unsaturated organosilicon monomer can be a disilazane of the formula $R'R''_2Si-NH-SiR''_2R'$ where $R'$ and $R''$ are as defined. The unsaturated organosilicon monomer can be a cyclic silazane of the formula $(R'R''SiNH)_3$ where $R'$ and $R''$ are as defined. A preferred unsaturated organosilicon monomer is vinyltriethoxysilane.

Examples of unsaturated organosilicon monomers include silanes such as $ViMeSiCl_2$, $ViMe_2SiOMe$, $ViMeSi(OEt)_2$, and $ViSi(OEt)_3$, siloxanes such as $(ViMe_2Si)_2O$, $(ViMeSiO)_3$, and $(ViMeSiO)_a$ where a is 3 to 6 inclusive, and silazanes such as $(ViMe_2Si)_2NH$ and $(ViMeSiNH)_3$ where Me is methyl radical, Et is an ethyl radical and Vi is vinyl radical.

The unsaturated organic monomer and the unsaturated organosilicon monomer can be emulsion polymerized by the common methods of performing such copolymerizations. One such process is described by Blackderf in U.S. Pat. No. 3,706,697, which is hereby incorporated by reference to show a process for copolymerizing an acrylic ester and an acryloxyalkylalkoxysilane by emulsion polymerization of the organic monomer through a free radical generator.

For example, a mixture is prepared of water and an anionic surfactant, and then a mixture of styrene and vinyltriethoxysilane is slowly added under a nitrogen blanket. Ammonium persulfate then is added as the polymerization catalyst. Heating the mixture initiates the polymerization, but it is also necessary to control the reaction temperature so that the emulsion does not overheat due to the exothermic reaction. After polymerization, the emulsion is adjusted to a pH of greater than 7.

The copolymer is added in amount of 5 to 100 parts by weight of the emulsion polymerized copolymer for each 100 parts by weight of polymerizable Si-containing compound, e.g. polydiorganosiloxane. The addition of the copolymer serves to act as a reinforcement or filler for the polydiorganosiloxane. Amounts of from 5 to 25 parts of copolymer added per 100 parts of polymerizable Si-containing compound yield a reinforced membrane having the desired glucosepermeability and strength without the addition of other fillers such as $SiO_2$. When the amount of copolymer added is from 25 to 60 parts by weight, the final product obtained by drying the emulsion is a higher strength membrane. The more copolymer added, the harder and less elastic the final membrane becomes.

In accordance with one embodiment of the invention, an alkyl tin salt is added to the dispersion to catalyze the curing of the final emulsion during the devolatilization or other removal of the carrier to yield the cured membrane. Preferred salts are dialkyltin dicarboxylates such as dibutyltindiacetate, dibutyltindilaurate, and dioctyltindilaurate. Most preferred is dibutyltindilaurate. The emulsion of catalyst is used in an amount sufficient to yield from 0.1 to 2 parts by weight of the alkyl tin salt for each 100 parts by weight of the polymerizable Si-containing compound, e.g., polydiorganosiloxane. Larger amounts could be used, but the larger amount would serve no useful purpose.

A silane cross-linking agent, of the general formula $A_m$-Si(OR)$_{4-m}$ can be added to the dispersion to enhance the physical properties of the cured carrier matrix. The radical A, in the silane cross-linking agent is a member selected from the group consisting of a hydrogen atom, monovalent hydrocarbon radicals containing 1 to 6 inclusive carbon atoms, and monovalent halohydrocarbon radicals containing 1 to 6 inclusive carbon atoms. Preferred radicals are methyl, ethyl, phenyl, and 3,3,3-trifluoropropyl with methyl being most preferred. The radical R is a hydrogen atom, or an alkyl group containing 1 to 4 inclusive carbon atoms, $-CH_2CH_2OC_2H_5$ group.

The R radicals on a silane molecule can be the same or different. The number of A radicals can be 0 or 1, meaning that a silane molecule can be either tri or tetra-functional in order to function as a cross-linker in the curing of the final membrane of this invention. The OR group on the silane is a hydrolyzable group that forms SiOH during curing of the membranes of this invention. The preferred silane cross-linking agent is methyltrimethoxysilane. The silane crosslinking agent can be included in a sufficient amount to obtain the desired degree of crosslinking. The amount to be used depends upon the hydroxyl content of the polymerizable Si-containing compound and the molecular weight of the crosslinking agent chosen. The more crosslinking agent used, the harder and less elastic the membrane becomes. Useful amounts of the preferred methyltrimethoxysilane cross-linker vary from 1 to 7 parts by weight of silane per 100 parts by weight of polydiorganosiloxane.

Other useful silicone containing compounds capable of polymerizing to form a carrier matrix layer having a homogeneously mixed reactant system included prior to complete curing and that is glucose-permeable after complete curing include the copolymers of diorganosiloxanes and any hydrolyzable silane, as disclosed in the Sorkin U.S. Pat. No. 3,624,017, hereby incorporated by reference.

The diorganosiloxanes can be included in the dispersion as a monomer or a polymer. The monomer can be partially polymerized in the dispersion or emulsion and then silane added and copolymerized with the diorganosiloxane polymer. The surfactant used to form an emulsion with the copolymers can be either anionic, cationic or nonionic and any catalyst useful to initiate the copolymerization can be used, such as a strong acid or a strong base. The starting diorganosiloxane can be either a cyclic or a linear material and the molecular weight of the starting diorganosiloxane is not critical.

The dispersion of the polymerizable silicon-containing compound or compounds can contain the components in a broad range of concentrations. The preferred concentration range will depend on the thickness of the carrier matrix desired. For example, to provide a 0.5 mm thick matrix that does not form cracks as the carrier or continuous phase evaporates, it is best to use a dispersion having a combined amount of silicate and polydiorganosiloxane in the range of 67 to 160 parts by weight for each 100 parts by weight of carrier, e.g., water. Preferred test strip thicknesses are 0.13 to 0.64 mm (0.5 to 25 mils), for example 0.11 mm (4.5 mils).

If an emulsifying agent is incorporated into the carrier matrix composition to form the dispersion, the amount of emulsifying agent can be less than 2 weight percent of the emulsion, and the emulsifying agent can result from neutralized sulfonic acid used in the emulsion polymerization method for the preparation of a hydroxyl endblocked polydiorganosiloxane.

Anionic surfactants are preferably the salt of the surface active sulfonic acids used in the emulsion polymerization to form the hydroxyl endblocked polydiorganosiloxane as shown in U.S. Pat. No. 3,294,725, hereby incorporated by reference to show the surface active sulfonic acids and salts thereof. The alkali metal salts of the sulfonic acids are preferred, particularly the sodium salts. The sulfonic acid can be illustrated by aliphatically substituted benzenesulfonic acids, aliphatically substituted naphthalene sulfonic acids, aliphatic sulfonic acids, silylalkylsulfonic acids and aliphatically substituted diphenylethersulfonic acids. Other anionic emulsifying agents can be used, for example, alkali metal sulforicinoleates, sulfonated glyceryl esters of fatty acids, salts of sulfonated monovalent alcohol esters, amides of amino sulfonic acid such as the sodium salt of oleyl methyltauride, sulfonated aromatic hydrocarbon alkali salts such as sodium alpha-naphthalene monosulfonate, condensation products of naphthalene sulfonic acids with formaldehyde, and sulfates such as ammonium lauryl sulfate, triethanol amine lauryl sulfate and sodium lauryl ether sulfate.

Nonionic emulsifying agents also can be included in the carrier matrix emulsion in addition to the anionic emulsifying agents. Such nonionic emulsifying agents are, for example, saponins, condensation products of fatty acids with ethylene oxide such as dodecyl ether of tetraethylene oxide, condensation products of ethylene oxide and sorbitan trioleate, condensation products of phenolic compounds having side chains with ethylene oxide such as condensation products of ethylene oxide with isododecylphenol, and imine derivatives such as polymerized ethylene imine.

The polymerizable silicon-compound dispersion used to form the glucose-permeable test strips of the present invention may contain additional ingredients to modify the properties of the dispersions or the cured polymeric membrane products obtained from the dispersion. For example, a thickener may be added to modify viscosity of the dispersion or to provide thixotropy for the dispersion. An antifoam agent may be added to the dispersion to reduce foaming during preparation, coating or curing in layer form.

Fillers may be added to the dispersion to reinforce, extend or pigment the membrane. Useful fillers include colloidal silica, carbon black, clay, alumina, calcium carbonate, quartz, zinc oxide, mica, titanium dioxide and others well known in the art. These fillers should be finely divided and it may be advantageous to use aqueous dispersions of such fillers if they are commercially available, such as aqueous dispersions of carbon black. The polymerizable Sicompound containing dispersions do not require a filler and such can be added in dry or aqueous forms to provide selected properties to the test strips.

The filler preferably has an average particle diameter of less than 10 micrometers Useful fillers have had average particle diameters ranging down to as low as 0.05 micrometer. When these silicone emulsions are spread out for final curing to form the glucose-permeable test devices of the present invention, the water or other nonsolvent carrier evaporates, or is otherwise removed, to leave a cured glucose and oxygen-permeable test device having a reactant system firmly and homogeneously immobilized throughout the carrier matrix for interaction with the test solution. Evaporation of the carrier is usually complete within a few minutes to about one day depending on the dispersion film thickness and method of application. Another of the important advantages of the present invention is the excellent adhesion shown by these matrix materials for both polar and nonpolar substrates if it is desired to cure the carrier matrix onto any suitable support layer, e.g. polyethylene terephthalate, for additional structural integrity.

It should be understood that this invention is not limited to removal of continuous liquid phase from the carrier matrix in the silicon dispersion by evaporation, since other methods such as coagulation may be useful. Heating the polymerizable silicon-containing dispersions to more rapidly remove the carrier to produce more rapidly cured membranes also may be advantageous.

In accordance with the present invention, the glucose-permeable polymeric carrier matrixes disclosed herein are useful in conjunction with any known reactive system dispersible in the matrix for a determination of the presence and/or concentration of any reactive component in a test sample.

The present invention contemplates in its broader aspects for glucose measurements an indicator comprising a glucose enzyme and a substance capable of undergoing a color change with one or more of the compounds formed during the catalytic action of the enzyme upon a reaction involving glucose. The compounds formed during the reaction involving glucose may in turn react with other substances which themselves undergo no or only a slight color change but which react with a color-forming substance to produce a color. More than one substance can mediate between the compounds formed during the reaction and the color-forming substance. Enzymes are biological catalysts and many of them have an unusual specificity for catalyzing a particular reaction with a single, specific and predetermined chemical substance. The glucose enzymes contemplated are those which will catalyze a reaction of glucose when contained in the liquid being tested, thereby producing a predetermined reaction product. The indicating substance is one capable of forming a color or changing color in the presence of a reaction product or a mediating substance. Any amount of the enzymes and color forming or changing components sufficient to cause a degree of reactant sufficient to produce a detectable change in the reactant system can be incorporated in the reactant system of the matrix. Suitable amounts of the glucose enzyme, e.g., glucose oxidase and a substance having peroxidative activity, e.g., horseradish peroxidase, are, for example, 1,000 to 100,000 units into about 20 grams of polymerizable silicon-containing matrix material. Suitable amount of color forming or color changing agents are, for example, 0.01% to 30% by weight of the total weight of matrix material and reactant system, on the dry basis, preferably 1 to 10% by weight. The pH of the matrix material and reactant system is, for example, 7 to 11, and preferably 8 to 10.

A color-forming substance is incorporated into the reactant system which will be oxidized or reduced by any hydrogen peroxide formed, or reduced by reduced flavin present in glucose oxidase, in the fluid medium as a result of reaction between glucose, glucose oxidase and oxygen to produce a colored material or a material of a different color from that of the original substance. The color-forming substance may undergo color change not as a result of direct action of the hydrogen peroxide but can be mediated through another compound which is acted upon by the hydrogen peroxide but which does not itself become highly colored.

In accordance with the preferred embodiment of the invention, the reactant system contains a dual enzyme system, one enzyme of which catalyzes the transformation of glucose to produce hydrogen peroxide, the other enzyme having peroxidase activity, said indicator also having present a color-forming substance which is sensitized when hydrogen peroxide is produced when glucose is present.

The preferred glucose indicator of the invention comprises glucose oxidase and peroxidase or a peroxidase-like substance having peroxidative activity, and a compound capable of forming color or changing color in the presence of hydrogen peroxide. When this reactant system contained in the matrix of the present invention comes into contact with glucose or a material containing glucose, such as the blood of a diabetic, the peroxidase catalyzes the reaction between hydrogen peroxide and the color changing compound to produce the oxidized form of the compound. The color changing compound can be any compound capable of producing a color or changing color upon being acted upon by hydrogen peroxide in the presence of the substance having peroxidative activity. More than one substance having peroxidative activity may be present in the reactant system. For example, sodium iodide can be present with tetramethylene benzidine or gum guaiac.

Color-forming substances of peroxidase and peroxidase-like substances which produce a color formation in the presence of hydrogen peroxide and a substance having peroxidative activity include the following substances:

(1) Monoamines, such as aniline and its derivatives, ortho-toluidine, para-toluidine, and the like.

(2) Diamines, such as ortho-phenylenediamine, N,N'-dimethyl-para-phenylenediamine, N,N'-diethyl phenylenediamine, benzidine and its derivatives, such as tetramethylene benzidine (which produces a blue or brown color), dianisidine (turns green or brown), and the like;

(3) Phenols, such as phenol per se (producing a yellow color), thymol, ortho-, meta and para-cresols (producing a green-yellow color, a pin color and a milky suspension, respectively), alpha-naphthol (producing a magenta color), beta-naphthol (producing a white precipitate), and the like.

(4) Polyphenols, such as catechol, guaiacol (which forms an orange color), orcinol, pyrogallol (producing a reddish or yellow color), p,p-dihydroxydiphenyl and phloroglucinol;

(5) Aromatic acids, such as salicylic, pyrocatechuic and gallic acids;

(6) Leuco dyes, such as leucomalachite green (to produce malachite green) and leucophenolphthalein (desirably employed in an alkaline medium);

(7) Colored dyes, such as 2,6-dichlorophenolindophenol.

(8) Various biological substances, such as epinephrine, the flavones, tyrosine, dihydroxyphenylalanine (producing an orange-reddish color) and tryptophane; and (9) Other substances, such as gum guaiac, guaiaconic acid, nadi reagent (producing a bluish color) potassium sodium, and other water soluble iodides; and bilirubin (producing a greenish color).

The glucose indicator of the invention can have incorporated therein a suitable buffer to provide a desired pH. The pH of the indicator is generally not critical and the most desirable pH range will vary somewhat depending upon the glucose enzyme and other components employed in the indicator. However, extremes of low and high pH values are to be avoided.

Typical substances having peroxidative activity include the plant peroxidases, such as horseradish peroxidase or potato peroxidase-iodide and molybdate salts such as potassium iodide and sodium molybdate; small measured portions of whole blood, red blood cells alone, lyophylized blood; urohemin and other porphyrin substances having peroxidative activity and other compounds or combinations of compounds, such as disclosed in U.S. Pat. Nos. 3,298,789 and 2,981,606, hereby incorporated by reference.

The carrier matrix disclosed herein is particularly useful with a reactive system containing a compound capable of catalyzing the reaction between glucose and oxygen, such as glucose oxidase or glucose dehydrogenase, where the resulting concentration of $H_2O_2$ formed in the following catalyzed reaction:

interacts with another reactive system component to produce a visually detectable color change in the carrier matrix. The color change is comparable to a color chart to determine the concentration of glucose in the blood sample placed onto and permeating the surface of the test device. While, in the prior art, such a measurement of glucose was less precise because of interactions by interfering reducing agents, such as ascorbic acid, the glucose-permeable test strips of the present invention are very selective to permeation of glucose and oxygen while preventing the permeation of sensitive reducing agents. Accordingly, the test strips of the present invention are also very well suited to such $H_2O_2$ measurement systems.

EXAMPLE

Figure 1:
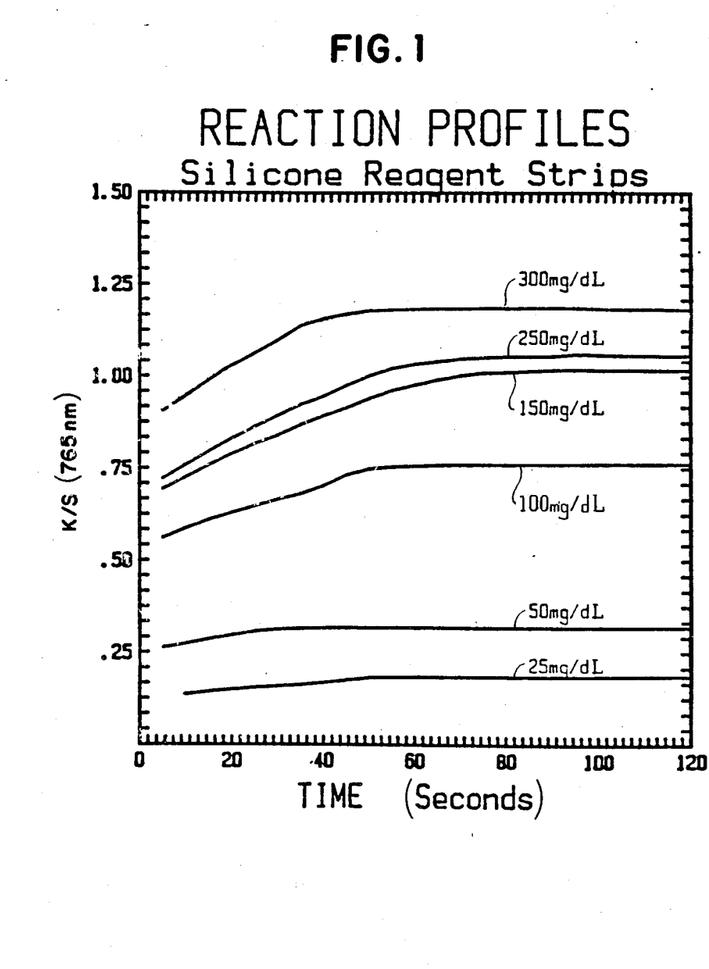
FIG. 1 is a graph showing reaction profiles of aqueous glucose solutions at various concentrations, in the reagent strips of the present invention.
Figure 2:
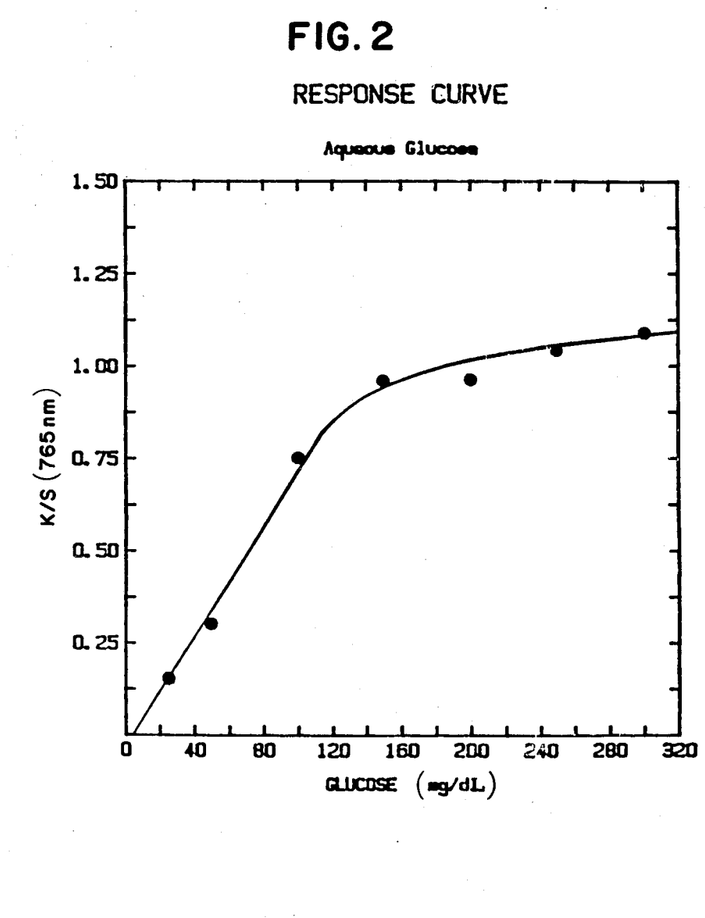
FIG. 2 is a graph showing the reaction response of aqueous glucose solutions at various glucose concentrations.
Figure 3:
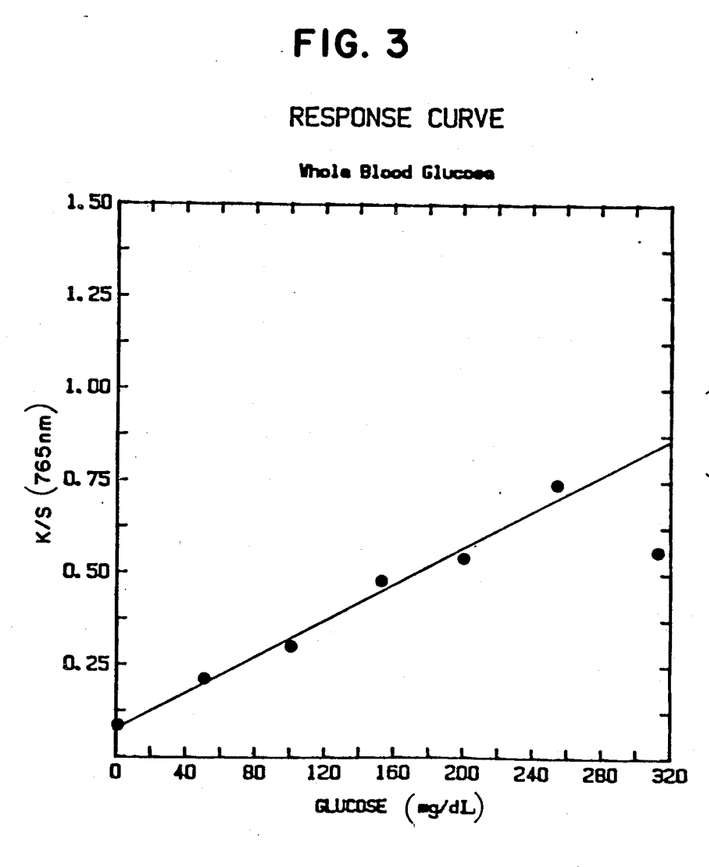
FIG. 3 is a graph, similar to FIG. 2, showing the reaction response of whole blood glucose at various glucose levels, showing that less glucose is absorbed into the pores of the reagent strip from whole blood, than from an aqueous glucose sample (FIG. 2)
Figure 4:
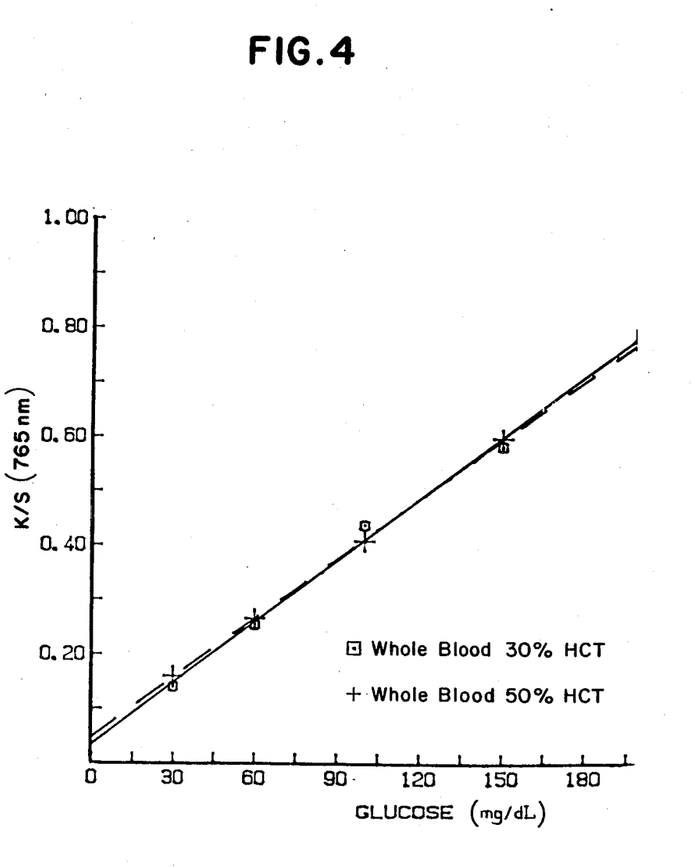
FIG. 4 is a graph showing the hematocrit independence of the test strip of the present invention, as essentially identical when measured at 30% hematocrit (HCT) and 50% HCT.

A test strip device was manufactured by mixing 40 grams of an anionically stabilized (3.8 parts by weight sodium lauryl sulfate and 0.8 parts by weight dodecyl benzene sulfonic acid), water-based hydroxyl endblocked polydimethyl-siloxane elastomer, having a weight average molecular weight, prior to curing, of about 325,000, containing about 5 percent by weight colloidal silica and 5 grams of finely ground $TiO_2$ dispersed in about 45% to 50% by weight water and adding thereto while mixing, the following reactant composition:

tetramethylbenzidine: 1 gm.
horseradish peroxidase: 5000 units
glucose oxidase: 5000 units
tris(hydroxymethyl) aminomethane (buffer): 0.12 gm.
water: 10 gms The pH of the carrier matrix composition containing the reactant composition is 8.5. The mixture, after sufficient mixing to insure a homogeneous blend, was cast onto a polyethylene terephthalate sheet for added structural integrity in a carrier matrix thickness of 10 mils. and dried at 50° C. for 20 minutes. The final dry thickness was about 4.5 mils. Portions of the test strip were tested with both aqueous glucose and whole blood yielding the results shown in FIGS. 1-4.

A surprising characteristic of the polymerized silicon-containing carrier matrix of the present invention is glucose-permeability which is contrary to the teaching of the prior art. The polymerizable matrix materials described herein are very compatible with whole blood, have a durable surface and are highly selective to oxygen penetration so that a sufficient stoichiometric excess of oxygen permeates the test devices even from whole blood.

The cured carrier matrix of the test device has a durable and resilient surface allowing it to be rinsed and wiped off after use to remove any colored blood components or other contaminants, such as proteins, that could build up and foul the matrix surface, thereby interfering with an accurate color comparison.

The preferred materials for the carrier matrix are an anionically stabilized, waterbased hydroxyl endblocked polydimethylsiloxane elastomer containing about 5 percent by weight colloidal silica sold by Dow Corning as elastomer and manufactured in accordance with Dow Corning U.S. Pat. No. 4,221,668. The preferred test strips are prepared by casting the elastomers onto a polyester, for example, polyethylene terephthalate, film with a 0.25 mm (10 mil.) doctor blade and curing at ambient conditions. Curing is accomplished in 30–60 minutes, but can be accelerated with heat, as shown in the example. This process gives a final dry matrix layer thickness of approximately 0.11 mm (4.5 mils.).

The test devices of the present invention can also be used to measure glucose in other body fluids such as sweat. To perform measurements of this type, the test device is placed in tight contact with the skin. The glucose permeability of the carrier matrix of the present invention is less than that of the skin. The color change in the reactant system will then be proportional to the blood glucose. One form for a glucose test strip operative on sweat would be a wrist watch type sensor having replaceable test strips and an adjacent standard color chart to determine glucose concentration. Conceptually, other advances in technology could also be incorporated such as alarms for high and low glucose or an alarm to remind the wearer that the time for insulin injection has come.

Many modifications and variations of the present invention are possible in light of the above teachings. Thus, it is to be understood that, within the scope of the appended claims, the invention may be practiced other than as specifically described.

What is claimed and sought to be secured by Letters Patent of the United States is:

1. A test article for detecting the relative concentration of glucose in a test fluid comprising a matrix layer polymerized from a polymerizable compound dispersed in a carrier liquid and having homogeneously incorporated therein a reagent system capable of reaction with glucose in said test fluid to produce a detectable change in said matrix layer, and wherein said polymerizable compound is a glucose permeable, silicone water-based elastomer compound.

2. The test article of claim 1 wherein said matrix layer, when dried, is impermeable to hemoglobin and other coloring bodies found in whole blood.

3. The test article of claim 1 wherein the reagent system comprises a catalyst capable of causing a reaction with glucose to produce hydrogen peroxide; a substance having peroxidative activity. and a compound capable of reaction to a colored form or reaction to change color in the presence of hydrogen peroxide and a material having peroxidative activity.

4. The test article of claim 3 wherein said catalyst is glucose oxidase or glucose dehydrogenase.

5. The test article of claim 1 wherein the glucose permeable, silocone water-based compound comprises an organosiloxane.

6. The test article of claim 5 wherein the organosiloxane compound comprises a diorganosiloxane.

7. The test article of claim 6 wherein the diorganosiloxane comprises a dimethylsiloxane.

8. The test article of claim 6 wherein the diorganosiloxane compound comprises an endblocked diorganosiloxane.

9. The test article of claim 8 wherein the endblocked diorganosiloxane compound comprises a vinyl or hydroxy endblocked diorganosiloxane.

10. A reagent strip for sensing the presence of a chemical compound in a liquid, comprising:
a silicone water-based polymerizable material permeable to a liquid chemical compound and including a reagent system incorporated homogeneously into the silicone water-based material, said reagent system including a catalyst capable of causing reaction of the chemical compound to produce $H_2O_2$, and a material capable of reaction with the $H_2O_2$ to produce a detectable color change in said silicone water-based material.

11. The reagent strip of claim 10 wherein said catalyst is glucose oxidase or glucose dehydrogenase.

12. The reagent strip of claim 10 wherein said silicone water-based polymerizable material is a silicone water-based elastomer.

13. An article for determining the relative concentration of glucose in a biological fluid comprising:
a glucose-permeable polymerized layer formed from a layer of a dispersed, polymerizable silicone water-based elastomer in a removable carrier liquid, said silicone elastomer being substantially immiscible in said carrier liquid, and a portion of said carrier liquid being removed during polymerization of said silicone elastomer in dispersed, layered form; and
a glucose reagent system incorporated into said layer of disperesed, polymerizable silicone water-based elastomer by mixing said reagent system into said carrier liquid.

14. A method of manufacturing a test article for determining the presence of a predetermined chemical compound in a test fluid comprising:
mixing a predetermined quantity of a reagent composition into an incompletely cured silicone polymerizable material dispersed in a removable carrier liquid to form a reagent containing matrix material;
forming said reagent-containing matrix material into a layer on a support surface; and
drying said layer and polymerizing said silicone polymerizable material on said support surface while removing said carrier liquid to form a dried matrix material layer permeable to a predetermined chemical compound and containing reagent composition capable of reaction with the predetermined chemical compound in a test fluid when the predetermined chemical compound penetrates into said dried matrix material layer;
wherein a catalyst is added to the reagent containing matrix material, said catalyst capable of causing a reaction with the predetermined chemical compound in the test fluid to produce hydrogen peroxide; a substance having peroxidative activity is added to the reagent containing matrix material; and a compound capable of reaction to a colored form or reaction to change color in the presence of hydrogen peroxide is added to the regaent containing matrix material.

15. The method of claim 14 wherein the test fluid comprises a biological fluid and the predetermined chemical compound comprises glucose, and said catalyst capable of causing a glucose reaction to form hydrogen peroxide is glucose oxidase.

16. The method of claim 14 wherein the predetermined chemical compound comprises an alcohol and said reagent system includes alcohol oxidase as a catalyst.

17. The method of claim 14 wherein the predetermined chemical compound comprises cholesterol and said reagent system includes cholesterol oxidase as a catalyst.

18. The method claim 14 wherein the predetermined chemical compound comprises uric acid and said reagent system includes urease as a catalyst.

19. The method of claim 14 wherein said catalyst is glucose oxidase or glucose dehydrogenase.

20. The method of claim 14 wherein the silicone polymerizable material comprises an organosiloxane.

21. The method of claim 20 wherein the organosiloxane material comprises a diorganosiloxane.

22. The method of claim 21 wherein the diorganosiloxane material comprises an endblocked diorganosiloxane.

23. The method of claim 21 wherein the diorganosiloxane material comprises a vinyl or hydroxy endblocked diorganosiloxane.

24. The method of claim 21 wherein the diorganosiloxane material comprises a dimethylsiloxane.

25. A method of measuring the concentration of a predetermined chemical compound in a test fluid comprising:
mixing a predetermined quantity of a reagent composition into an incompletely cured silicone polymerizable material dispersed in a removable carrier liquid to form a reagent-containing matrix material permeable to a predetermined chemical compound in a test fluid;
forming said reagent-containing matrix material into a layer; and
drying said layer and polymerizing said polymerizable material while removing said carrier liquid to form a dried matrix material layer permeable to said predetermined chemical compound and containing a reagent composition capable of reaction with said predetermined chemical compound when said predetermined chemical compound penetrates into said dried matrix material layer;

contacting a surface of said dried matrix material layer with said test fluid to cause a visibly detectable color change in said matrix material layer; and determining the concentration of said predetermined chemical compound based upon the degree of said color change.

26. The method of claim 25 wherein said test fluid is whole blood.

27. The method of claim 26 further including wiping or washing the test fluid contacted surface to remove any substantial amount of hemoglobin and other coloring bodies found in said whole blood prior to determining the color change.

28. A method of manufacturing a test device including a continuous layer of a silicone containing polymer permeable to a predetermined chemical compound while screening out hemoglobin and other coloring bodies found in whole blood comprising:

dispersing a polymerizable silicone containing compound in removable carrier liquid to form an incompletely cured polymerizable layer forming composition, said silicone containing compound being substantially immiscible in said carrier liquid;

adding a reagent composition to said polymerizable layer forming a composition capable of interaction with a predetermined chemical compound to produce a detectable color change in said polymerizable layer;

applying said incompletely cured polymerizable layer forming composition containing said reagent composition onto a support surface; and polymerizing said silicone containing compound while in layer form and removing at least a portion of the carrier liquid during polymerization of the silicone containing compound in dispersed, layered form, to form a cured, continuous polymerized silicone containing compound layer permeable to said predetermined chemical compound.

29. The method of claim 28 including stripping the polymerized silicone containing compound layer from said support surface.

30. The method of claim 28 wherein said support surface comprises a continuous sheet of polyethylene terephthalate.

31. The method of claim 28 including adding a polymerization initiator to said incompletely cured polymerizable layer forming composition and heating said polymerizable layer forming composition to temperature above above ambient to remove the carrier liquid during polymerization.

32. The method of claim 28 including adding an emulsifying agent to said incompletely cured membrane composition and emulsifying said polymerizable layer forming composition prior to applying said incompletely cured polymerizable layer onto the support layer.

33. The method of claim 28 wherein the carrier liquid comprises at least 5% by weight of the incompletely cured polymerizable layer forming composition prior to completion of polymerization.

34. The method of claim 28 wherein the polymerizable silicone containing compound is an organosiloxane.

35. The method of claim 34 wherein the organosiloxane compound is a diorganosiloxane.

36. The method of claim 35 wherein the diorganosiloxane is a dimethylpolysiloxane.

37. The method of claim 35 wherein the diorganosiloxane compound is an endblocked diorganosiloxane.

38. The method of claim 37 wherein the endblocked diorganosiloxane compound is a vinyl or hydroxy endblocked diorganopolysiloxane.

* * * * *